United States Patent [19]
Gajda et al.

[11] Patent Number: 6,114,592
[45] Date of Patent: Sep. 5, 2000

[54] SELECTIVE AROMATICS DISPROPORTIONATION PROCESS

[75] Inventors: Gregory J. Gajda, Mount Prospect; Edwin P. Boldingh, Arlington Heights, both of Ill.

[73] Assignee: UOP LLC, Des Plaines, Ill.

[21] Appl. No.: 09/213,957

[22] Filed: Dec. 17, 1998

[51] Int. Cl.[7] ...................................... C07C 5/22
[52] U.S. Cl. ........................................... 585/475; 585/470
[58] Field of Search ..................... 585/475, 470

[56] References Cited

U.S. PATENT DOCUMENTS

| | | | |
|---|---|---|---|
| 2,778,863 | 1/1957 | Maisel et al. | 260/674 |
| 4,011,276 | 3/1977 | Chu | 260/672 T |
| 4,016,219 | 4/1977 | Kaeding | 260/672 T |
| 4,097,543 | 6/1978 | Haag et al. | 260/672 T |
| 4,182,923 | 1/1980 | Chu | 585/475 |
| 4,629,717 | 12/1986 | Chao | 502/208 |
| 4,795,550 | 1/1989 | Sachtler et al. | 208/307 |
| 5,169,812 | 12/1992 | Kocal et al. | 502/61 |

*Primary Examiner*—Walter D. Griffin
*Assistant Examiner*—Thuan D. Dang
*Attorney, Agent, or Firm*—John G. Tolomei; John F. Spears, Jr.; Richard E. Conser

[57] ABSTRACT

An improved process combination is disclosed for the selective disproportionation of toluene. The combination comprises selective hydrogenation of a toluene feedstock followed by disproportionation using a zeolitic catalyst which is oil-dropped in an aluminum phosphate binder to achieve a high yield of paraxylene. Optionally, the catalyst is selectively precoked prior to toluene disproportionation. The catalyst and process provide improved selectivity for the production of paraxylene.

18 Claims, No Drawings

SELECTIVE AROMATICS DISPROPORTIONATION PROCESS

BACKGROUND OF THE INVENTION

This invention relates to processes for the conversion of aromatic hydrocarbons, and is more specifically directed to an improved process for disproportionation and transalkylation of aromatic hydrocarbons to obtain xylenes.

The xylene isomers are produced in large volumes from petroleum as feedstocks for a variety of important industrial chemicals. The most important of the xylene isomers is paraxylene, the principal feedstock for polyester which continues to enjoy a high growth rate from large base demand. Orthoxylene is used to produce phthalic anhydride, which has high-volume but mature markets. Metaxylene is used in lesser but growing volumes for such products as plasticizers, azo dyes and wood preservers. Ethylbenzene generally is present in xylene mixtures and is occasionally recovered for styrene production, but usually is considered a less-desirable component of $C_8$ aromatics.

Among the aromatic hydrocarbons, the overall importance of the xylenes rivals that of benzene as a feedstock for industrial chemicals. Neither the xylenes nor benzene are produced from petroleum by the reforming of naphtha in sufficient volume to meet demand, and conversion of other hydrocarbons is necessary to increase the yield of xylenes and benzene. Most commonly, toluene is dealkylated to produce benzene or disproportionated to yield benzene and $C_8$ aromatics from which the individual xylene isomers are recovered. More recently, processes have been introduced to disproportionate toluene selectively to obtain higher-than-equilibrium yields of paraxylene.

A current objective of many aromatics complexes is to increase the yield of xylenes and to deemphasize benzene production. Demand is growing faster for xylene derivatives than for benzene derivatives. Refinery modifications are being effected to reduce the benzene content of gasoline in industrialized countries, which will increase the supply of benzene available to meet demand. Benzene produced from disproportionation processes often is not sufficiently pure to be competitive in the market. A higher yield of xylenes at the expense of benzene thus is a favorable objective, and processes to transalkylate $C_9$ aromatics along with toluene have been commercialized to obtain high xylene yields.

U.S. Pat. No. 4,016,219 (Kaeding) discloses a process for toluene disproportionation using a catalyst comprising a zeolite which has been modified by the addition of phosphorus in an amount of at least 0.5 mass-%. The crystals of the zeolite are contacted with a phosphorus compound to effect reaction of the zeolite and phosphorus compound. The modified zeolite then may be incorporated into indicated matrix materials.

U.S. Pat. No. 4,097,543 (Haag et al.) teaches toluene disproportionation for the selective production of paraxylene using a zeolite which has undergone controlled precoking. The zeolite may be ion-exchanged with a variety of elements from Group IB to VIII, and composited with a variety of clays and other porous matrix materials.

U.S. Pat. No. 4,629,717 (Chao) discloses a phosphorus-modified alumina hydrogel formed by gelation of a homogeneous hydrosol. The composite has a relatively high surface area of 140–450 $m^2/g$ and high activity and selectivity in 1-heptene conversion tests.

U.S. Pat. No. 4,795,550 (Sachtler et al.) teaches removal of trace olefins from aromatics by alkylating the olefins with aromatics, using a catalyst comprising a zeolite and refractory inorganic oxide.

U.S. Pat. No. 5,169,812 (Kocal et al.) teaches a catalyst for aromatization of light hydrocarbons comprising a zeolite, preferably ZSM-5, a gallium component and an aluminum phosphate binder. The composite is treated with a weakly acidic solution, dried and calcined to increase its tolerance to hydrogen at high temperatures.

Workers in the field of aromatics disproportionation continue to seek processes and catalysts having exceptionally high selectivity for paraxylene from toluene combined with favorable activity and stability.

SUMMARY OF THE INVENTION

It is an object of the present invention to provide an improved process for the disproportionation of aromatic hydrocarbons to yield desirable alkylaromatic isomers. A specific objective is to obtain a high yield of paraxylene by catalytic disproportionation of toluene with long catalyst life.

This invention is based on the discovery that high catalyst activity and stability along with selectivity to paraxylene is obtained by disproportionation of toluene using a catalyst comprising a zeolite oil-dropped with an aluminum phosphate binder to process a feed which has been selectively hydrogenated.

The present invention therefore is directed to a process combination for the disproportionation of toluene to yield paraxylene comprising selective unsaturates removal from a toluene feedstock followed by disproportionation using an oil-dropped spherical disproportionation catalyst comprising a zeolitic aluminosilicate having a pore diameter of from about 5 to 8 Å and an aluminum phosphate binder. Removal of unsaturates from the feedstock preferably is effected by selective hydrogenation. The disproportionation catalyst of the present invention comprises a zeolitic aluminosilicate preferably selected from MFI, MEL and MTW, and most preferably comprises MFI. This catalyst preferably is subjected to a precoking step prior to its use for disproportionation in order to increase its selectivity to paraxylene in the product.

Preferably the product contains paraxylene in excess of its equilibrium concentration at disproportionation conditions. A process combination optionally comprises a xylene-separation-zone comprising crystallization and/or adsorption.

These as well as other objects and embodiments will become apparent from the detailed description of the invention.

DESCRIPTION OF THE PREFERRED EMBODIMENTS

A broad embodiment of the present invention therefore is directed to the disproportionation of a toluene feedstock, from which unsaturates have been removed, to obtain a paraxylene-rich product. The disproportionation preferably is effected using an oil-dropped spherical catalyst comprising a zeolitic aluminosilicate having a pore diameter of from about 5 to 8 Å and an aluminum phosphate binder. The paraxylene content of the product preferably is in excess of its equilibrium concentration at disproportionation conditions. Other embodiments of the invention encompass but are not limited to parameters such as incremental and alternative feedstocks, catalyst composition, catalyst conditioning for paraxylene selectivity, operating conditions and product recovery.

In a broad embodiment, the feedstock to the subject process comprises high-purity aromatic hydrocarbons derived from one or more sources. Aromatics may be produced synthetically, for example, from naphtha by catalytic reforming or aromatization or by pyrolysis followed by hydrotreating to yield an aromatics-rich product. An aromatics-containing feedstock may be derived from such product with suitable purity by extraction of aromatic hydrocarbons from a mixture of aromatic and nonaromatic hydrocarbons and fractionation of the extract. Large quantities of aromatic hydrocarbons are recovered commercially in this manner. For instance, aromatics may be recovered from a reformate through the use of a selective solvent, such as one of the sulfolane type, in a liquid—liquid extraction zone. When the severity of reforming or pyrolysis is sufficiently high, extraction may be unnecessary and fractionation may be sufficient to prepare the feedstock which should contain no more than about 10 mass-% and preferably less than about 1 mass-% nonaromatics. The recovered aromatics may then be separated into streams having the desired carbon number range by fractionation. The aromatic hydrocarbons may comprise one or more of toluene, xylene isomers, ethylbenzene, or $C_9$ and heavier aromatics. A preferred toluene feedstock prepared in this manner usually is fractionated to separate benzene and $C_8$ aromatics, and the degree of fractionation may be adjusted in accordance with economic factors of the disproportionation process.

The aromatics feedstock generally contains a small proportion of unsaturates in an amount depending on the reforming feed, severity and operating conditions and generally is between about 0.2 and 3 mass %, and more usually from about 0.3 to 2.5 mass %. The unsaturates generally comprise olefins, especially cycloolefins such as substituted cyclopentenes, and sometimes comprise trace amounts of diolefins and acetylenes such as substituted cyclopentadienes which are particularly troublesome in a disproportionation process. The unsaturates may be removed from the feedstock in a selective unsaturates-removal zone using any suitable method known in the art, including but not limited to clay treating, adsorption, extraction and selective hydrogenation.

Clay treating is one means of removing highly unsaturated hydrocarbons from the feed stream. The feed stream is contacted with a clay comprising principally amorphous combinations of silica and alumina such as Fuller's earth, Attapulgas clay, activated bentonite, Superfiltrol, Floridin and the like. Suitable operating conditions include a temperature of from about 150° to 400° C., a pressure of from atmospheric to about 50 atmospheres, and a weight hourly space velocity of from about 1 to 100. The acetylenes and dienes form polymer, which may remain on the clay or be removed from the product by fractional distillation.

Preferably, the selective unsaturates-removal zone is a selective-hydrogenation zone in which the feedstock contacts free hydrogen at selective-hydrogenation conditions. The selective-hydrogenation zone hydrogenates generally more than about 50%, more usually at least about 70%, and often 80% or more of olefins in the aromatics-rich product at relatively mild conditions to avoid saturation of aromatics. The feedstock generally contains between about 40 and 90 mass-% aromatics, and more usually between about 50 and 80 mass-%, depending upon the nature of the feed to the reforming step from which it preferably was derived and the severity of the reforming conditions. Aromatics saturation, which principally yields naphthenes, is controlled according to the present invention to less than about 1 mass % of the aromatics in the feed; preferably essentially no net aromatic saturation occurs.

The selective-hydrogenation zone contains a selective-hydrogenation catalyst which suitably comprises a supported Group VIII (IUPAC 8-10) metal. Contacting within the selective-hydrogenation zone may be effected using the catalyst in a fixed-bed system, a moving-bed system, a fluidized-bed system, or in a batch-type operation. In view of the danger of attrition loss of the valuable catalyst and of operational advantages, it is preferred to use a fixed-bed system. The catalyst generally is contained in a single reactor, as the low level of olefins in the feed generally does not warrant multiple reactors with intermediate temperature control. The reactants may be contacted with the bed of catalyst particles in either upward, downward, or radial flow fashion. The reactants may be in the liquid phase, a mixed liquid-vapor phase, or a vapor phase when contacted with the catalyst particles; mixed liquid-vapor contacting is preferred. The combined feed is preheated by suitable heating means which preferably comprises heat exchange to the desired reaction temperature and then passed into a reactor containing the bed of catalyst.

Operating conditions in the selective-hydrogenation zone include pressures from about 100 kPa to 6 MPa absolute, preferably between about 300 kPa and 3.5 MPa, and more preferably consistent with the associated disproportionation step. Temperature for selective olefin hydrogenation is between about 30° and 300° C. and more usually from about 60° to 250° C., and this generally can be effected via heat exchange within the disproportionation circuit of exchangers. The weight hourly space velocity (LHSV) ranges from about 1 to 100 $hr^{-1}$, preferably up to about 40 $hr^{-1}$.

Hydrogen to hydrocarbon ratios are established to effect selective hydrogenation of olefins with little or minimal aromatics saturation, considering the content of olefins in the olefin-containing aromatics-rich intermediate. The hydrogen usually is provided to be present in a range of about 0.5 to 20 moles per mole of double bonds present. If the only unsaturates in the feedstock present consist essentially of olefins; the moles of double bonds correspond to the moles of olefins; one mole of diolefins corresponds to two moles of double bonds. More usually, the molar ratio of hydrogen to double bonds is between about 1 and 5, and optimally no more than about 2. Assuming but not limiting the invention to a range of feedstock olefin contents of 0.07–0.2 mole %, the molar ratio of hydrogen to toluene feedstock usually is in the range of about 0.004 to 0.04, and more usually from about 0.007 to 0.01.

The selective-hydrogenation catalyst comprises a Group VIII (IUPAC 8-10) metal component supported on an inorganic-oxide binder. The refractory inorganic-oxide support suitably is a porous, adsorptive, high-surface-area support which is uniform in composition and relatively refractory to the conditions utilized in the process. The support typically comprises one or more of alumina, titania, zirconia, chromia, zinc oxide, magnesia, thoria, boria, silica-alumina, silica-magnesia, chromia-alumina, alumina-boria, silica-zirconia and others known in the art.

The preferred refractory inorganic oxide for use in the present invention comprises one or more of gamma-, eta-, and theta-alumina, with gamma- or eta-alumina giving best results A particularly preferred alumina is an extremely high purity pseudo-boehmite powder which, after calcination, has been shown to yield a high-purity gamma-alumina; this has been characterized in U.S. Pat. Nos. 3,852,190 and 4,012,313 as a byproduct from a Ziegler higher alcohol synthesis reaction as described in Ziegler's U.S. Pat. No. 2,892,858. For purposes of simplification, such an alumina will be hereinafter referred to as a "Ziegler alumina." Ziegler alumina is presently available from the Vista Chemical Company under the trademark "Catapal" or from Condea Chemie GMBH under the trademark "Pural."

The alumina powder may be formed into a suitable catalyst material according to any of the techniques known to those skilled in the catalyst-carrier-forming art to form shapes such as rods, pills, pellets, tablets, granules, extrudates. The preferred form of carrier material for the selective-hydrogenation catalyst is a cylindrical extrudate. An extruded shape is typically prepared by mixing the alumina powder with water and peptizing agents such as nitric acid, acetic acid, aluminum nitrate, and the like material until an extrudable dough is formed which then is extruded through a suitably sized die to form extrudate particles. The particles are dried at a temperature of about 150° to about 200° C. and calcined at a temperature of about 450° to 800° C. for a period of 0.5 to 10 hours to effect the preferred form of the refractory inorganic oxide.

An essential component of the preferred selective-hydrogenation catalyst is a Group VIII (IUPAC 8-10) metal, preferably a platinum-group metal or nickel. Of the preferred platinum group, i.e., platinum, palladium, rhodium, ruthenium, osmium and iridium, palladium is a favored component and platinum is especially preferred. Mixtures of platinum-group metals also are within the scope of this invention. This component may exist within the final catalytic composite as a compound such as an oxide, sulfide, halide, or oxyhalide, in chemical combination with one or more of the other ingredients of the composite, or, preferably, as an elemental metal. This component may be present in the final catalyst composite in any amount which is catalytically effective, generally comprising about 0.01 to 2 mass % of the final catalyst calculated on an elemental basis. Excellent results are obtained when the catalyst contains from about 0.05 to 1 mass % of platinum.

The platinum-group metal component may be incorporated into the selective-hydrogenation catalyst in any suitable manner such as coprecipitation or cogellation with the carrier material, ion exchange or impregnation. Impregnation using water-soluble compounds of the metal is preferred. Typical platinum-group compounds which may be employed are chloroplatinic acid, ammonium chloroplatinate, bromoplatinic acid, platinum dichloride, platinum tetrachloride hydrate, tetraamine platinum chloride, tetraamine platinum nitrate, platinum dichlorocarbonyl dichloride, dinitrodiaminoplatinum, palladium chloride, palladium chloride dihydrate, palladium nitrate, etc. Chloroplatinic acid is preferred as a source of the especially preferred platinum component.

It is within the scope of the present invention that the catalyst may contain other metal components known to modify the effect of the platinum-group metal component. Such metal modifiers may include, for example, rhenium, tin, germanium, lead, cobalt, nickel, indium, gallium, and mixtures thereof, with the Group IVA (IUPAC 14) metals being preferred. Catalytically effective amounts of such metal modifiers may be incorporated into the catalyst by any means known in the art.

The composite usually is dried at a temperature of about 100° to 300°, followed by calcination or oxidation at a temperature of from about 375° to 600° C. in an air or oxygen atmosphere for a period of about 0.5 to 10 hours in order to convert the metallic components substantially to the oxide form. The resultant oxidized catalytic composite then is subjected to a substantially water-free and hydrocarbon-free reduction step at conditions including a temperature of about 425° C. to about 650° C. and a period of time of about 0.5 to 2 hours. This step is designed to selectively reduce the platinum-group component to the corresponding metal and to insure a finely divided dispersion of the metal component throughout the carrier material.

The selective-hydrogenation zone produces a stable intermediate which usually passes directly to the disproportionation zone in the same hydrogen circuit without separation of hydrocarbon components. Temperature preferably is adjusted thorough heat exchange or heating for the generally higher temperature of the disproportionation zone. It is within the scope of the invention that fractionation optionally separates residual light gases prior to disproportionation. The stable intermediate, usually in admixture with toluene recycled from the products of the disproportionation reaction, is preferably admixed with free hydrogen to effect a combined feed to a disproportionation zone. If present, the hydrogen need not exceed a 20:1 molar ratio to feedstock hydrocarbons to effect satisfactory stability in the disproportionation reaction, and preferably is in the range of from about 0.5 to 10 molar ratio. The hydrogen may contain hydrocarbons, such as methane and ethane, and inerts such as nitrogen, but preferably is in a concentration of at least about 90 mole-% to avoid large hydrogen losses and unfavorable process economics. The disproportionation reaction yields a paraxylene-rich product which usually also comprises benzene, other $C_8$ aromatics, and smaller amounts of $C_9$+ aromatics.

The combined feed to the disproportionation zone usually is first heated by indirect heat exchange against the effluent of the reaction zone and is then further heated in a fired heater. The resulting vaporous stream is then passed through a reaction zone which may comprise one or more individual reactors. The use of a single reaction vessel having a fixed cylindrical bed of catalyst is preferred, but other reaction configurations utilizing moving beds of catalyst or radial-flow reactors may be employed if desired. Passage of the combined feed through the reaction zone effects the production of a vaporous effluent stream comprising hydrogen and both product and unconverted feed hydrocarbons. This effluent is normally cooled by indirect heat exchange against the stream entering the reaction zone and then further cooled through the use of air or cooling water. The temperature of the effluent stream generally is lowered by heat exchange sufficiently to effect the condensation of substantially all of the feed and product hydrocarbons having six or more carbon atoms per molecule. The resultant mixed-phase stream is passed into a vapor-liquid separator wherein the two phases are separated and from which the hydrogen-rich vapor is recycled to the reaction zone. The condensate from the separator is passed into a stripping column in which substantially all $C_5$ and lighter hydrocarbons present in the effluent are concentrated into an overhead stream and removed from the process. An aromatics-rich stream which is referred to herein as the disproportionation effluent stream is recovered as net stripper bottoms.

The catalyst preferably is subjected to precoking as described hereinbelow to increase the proportion of paraxylene in the $C_8$ aromatics product above equilibrium levels at disproportionation conditions.

Conditions employed in the disproportionation zone of the subject process normally include a temperature of from about 200° to 600° C., and preferably from about 350° to 575° C. The temperature required to maintain the desired degree of conversion will increase as the catalyst gradually loses activity during processing. Normal end-of-run temperatures may therefore exceed start-of-run temperatures by 65° C. or more. In the transalkylation embodiment wherein toluene and $C_9$ aromatics are present in the combined feed, reaction temperatures generally are somewhat lower within the range of about 200° to 525° C.

The disproportionation zone is operated at moderately elevated pressures broadly ranging from about 100 kPa to 6 MPa absolute. A preferred pressure range is from 2 to 3.5 MPa. The disproportionation reaction can be effected over a wide range of space velocities, with higher space velocities effecting a higher ratio of paraxylene at the expense of conversion. Weight hourly space velocity generally is the range of from about 0.2 to 10 $hr^{-1}$.

It is within the scope of the invention that the combined feed includes a heavy-aromatics stream comprising $C_9$ aromatics as a component of the combined feed to the present process. Transalkylation of toluene and $C_9$ aromatics is effected thereby within the disproportionation conditions described hereinabove. The heavy-aromatics stream may be derived from the same or different known refinery and petrochemical processes as the toluene feedstock and/or may be recycled from the separation of the product from disproportionation/transalkylation. Benzene also may be present in the combined feed to disproportionation/transalkylation. However, it is preferred that the feedstock consists essentially of toluene in order to effect a high degree of paraxylene selectivity as described hereinbelow.

The disproportionation effluent stream is separated into a light recycle stream, a paraxylene-rich mixed-$C_8$-aromatics product and a heavy-aromatics stream. The paraxylene-rich product may be sent to a xylene separation zone for recovery of pure paraxylene; optionally, other xylenes and ethylbenzene also may be recovered as pure products. The paraxylene-rich stream preferably contains paraxylene in proportion to total xylenes in excess of its equilibrium concentration at disproportionation conditions, more preferably at least about 80 mass-% paraxylene, and most preferably at least about 85 mass-% paraxylene. The light recycle stream may be diverted to other uses such as to benzene and toluene recovery, but optionally a portion is recycled to the disproportionation zone since it contains not only benzene and toluene but also amounts of nonaromatics which would remain with the benzene and reduce its commercial value. The heavy recycle stream contains substantially all of the $C_9$ and heavier aromatics and may be either withdrawn as a product of the process or partially or totally recycled to the reaction if transalkylation is an objective of the process.

The xylene-separation zone may utilize one or more different separation techniques such as fractionation, crystallization or selective adsorption to recover pure paraxylene from the paraxylene-rich stream in the xylene-separation zone. Conventional crystallization is disclosed in U.S. Pat. No. 3,177,255, U.S. Pat. No. 3,467,724 and U.S. Pat. No. 3,662,013. Various other crystallization alternatives are discussed in U.S. Pat. No. 5,329,061, incorporated by reference. In an embodiment in which the paraxylene-rich product has a paraxylene content substantially in excess of the equilibrium concentration, recovery of pure paraxylene may be effected using only a single stage of crystallization corresponding to the higher-temperature purification stage of conventional crystallization.

An alternative separation zone comprises a bed of molecular sieves operated in accordance with the teaching of U.S. Pat. No. 3,201,491 to simulate the use of a continuously moving bed of molecular sieves. Subsequent improvements to the process are described in U.S. Pat. No. 3,696,107 and U.S. Pat. No. 3,626,020. Details on the operation of the xylene-separation zone may also be obtained from U.S. Pat. No. 4,039,599 and U.S. Pat. No. 4,184,943. The simulated cocurrent adsorptive separation process of U.S. Pat. No. 4,402,832 may be employed. The extract and raffinate streams may be handled as described in these references or as described in U.S. Pat. No. 4,381,419.

The skilled routineer will recognize variations in the process combination described above which are within the scope of the invention. For example, benzene as well as toluene may be charged to the disproportionation zone as a supplementary feedstock. The xylene-separation zone may use one or more of several known separation techniques such as adsorption, crystallization and fractionation. Orthoxylene and/or metaxylene may be recovered by one or more of such techniques as pure products from the xylene-separation zone.

The process of the present invention comprises a molecular sieve and a refractory inorganic oxide. The preferred molecular sieves are zeolitic aluminosilicates, or zeolites, which may be any of those which have a $Si:Al_2$ ratio greater than about 10, preferably greater than 20, and a pore diameter of about 5 to 8 Angstroms (Å). Specific examples of zeolites which can be used are the MFI, MEL, EUO, FER, MFS, MTT, MTW, TON, MOR and FAU types of zeolites. Pentasil zeolites MFI, MEL, MTW and TON are preferred, and MFI-type zeolite, often designated ZSM-5, is especially preferred.

The preparation of the preferred MFI-type zeolite is well known in the art. The zeolite preferably is prepared by crystallizing a mixture containing an alumina source, a silica source, an alkali metal source, water and an alkyl ammonium compound or its precursor.

Preferably the zeolitic aluminosilicate, or zeolite, has an enhanced surface silicon content, i.e., the proportion of silicon at the surface of the zeolite is greater than the proportion in the bulk of the zeolite. The "surface" is defined for purposes of the present invention as a layer at the external surface of the zeolite which is less than about 100 angstroms in depth, and usually about 10 angstroms or less in depth. Optimally the silicon/aluminum ratio, expressed as $Si/Al_2$, is increased by about 5 or more at the surface of the zeolite relative to the ratio in the bulk of the zeolite. Elemental surface analysis to assess component ratios is effected by any suitable method as taught in the art, e.g., XPS, Auger spectroscopy or SIMS. XPS, or x-ray photoelectron spectroscopy, is particularly effective in determining surface ratios of framework components.

An enhanced surface silicon content is effected by treating the zeolite with a dilute acid solution or an aqueous solution of a weakly acidic ammonium salt, either as the bound zeolite or preferably before being composited with a binder. Preferred dilute acids for treating the unbound zeolite include hydrochloric, acetic, nitric, phosphoric and especially sulfuric acids. Ammonium salts which can be used include ammonium chloride, ammonium acetate, and especially ammonium nitrate for treating the bound zeolite. The treating solution is contacted with dried catalyst particles at a temperature of from about 50° to 100° C. for a period of from about 1 to 48 hours, and the particles then are separated, dried, and calcined at a temperature of from about 500° to 700° C. for a period of from about 1 to 15 hours.

A refractory binder or matrix is utilized to facilitate fabrication of the disproportionation catalyst, provide strength and reduce fabrication costs. The binder should be uniform in composition and relatively refractory to the conditions used in the process. Suitable binders include inorganic oxides such as one or more of alumina, magnesia, zirconia, chromia, titania, boria, thoria, zinc oxide and silica. Alumina and/or silica are preferred binders. The amount of zeolite present in the bound catalyst can vary considerably but usually is present in an amount from about 30 to 90 mass percent and preferably from about 50 to 80 mass percent of the catalyst. In a preferred embodiment, the catalyst consists essentially of the zeolite and binder.

A preferred binder or matrix component is a phosphorus-containing alumina (hereinafter referred to as aluminum phosphate) component. The phosphorus may be composited with the alumina in any acceptable manner known in the art. The zeolite and aluminum phosphate binder are mixed and formed into particles by means well known in the art such as gellation, pilling, nodulizing, marumerizing, spray drying, extrusion or any combination of these techniques. A preferred method of preparing the zeolite/aluminum phosphate support involves adding the zeolite either to an alumina sol or a phosphorus compound, forming a mixture of the alumina sol/zeolite/phosphorus compound into particles by employing an oil-drop method as described hereinbelow and calcining the spherical particles.

The preferred oil-drop method of preparing the aluminum phosphate is described in U.S. Pat. No. 4,629,717 which is incorporated by reference. The technique described in the '717 patent involves the gellation of a hydrosol of alumina which contains a phosphorus compound using the well-known oil-drop method. Generally this technique involves preparing a hydrosol by digesting aluminum in aqueous hydrochloric acid at reflux temperatures of about 80° to 105° C. The ratio of aluminum to chloride in the sol ranges from about 0.7:1 to 1.5:1 mass ratio. A phosphorus compound is now added to the sol. Preferred phosphorus compounds are phosphoric acid, phosphorous acid and ammonium phosphate. The relative amount of phosphorus and aluminum expressed in molar ratios ranges from about 10:1 to 1:100, respectively, on an elemental basis. The zeolite is added to the aluminum phosphate hydrosol and the mixture is gelled. One method of gelling this mixture involves combining a gelling agent with the mixture and then dispersing the resultant combined mixture into an oil bath or tower which has been heated to elevated temperatures such that gellation occurs with the formation of spheroidal particles. The gelling agents which may be used in this process are hexamethylene tetraamine, urea or mixtures thereof. The gelling agents release ammonia at the elevated temperatures which sets or converts the hydrosol spheres into hydrogel spheres. The combined mixture preferably is dispersed into the oil bath in the form of droplets from a nozzle, orifice or rotating disk. The spheres are then continuously withdrawn from the oil bath and typically subjected to specific aging and drying treatments in oil and in ammoniacal solution to further improve their physical characteristics. The resulting aged and gelled particles are then washed and dried at a relatively low temperature of about 100° to 150° C. and subjected to a calcination procedure at a temperature of about 450° to 700° C. for a period of about 1 to 20 hours,.

Alternatively, the particles may be formed by spray-drying of the mixture at a temperature of from about 425° to 760° C. In any event, conditions and equipment should be selected to obtain small spherical particles; the particles preferably should have an average diameter of less than about 1.0 mm, more preferably from about 0.2 to 0.8 mm, and optimally from about 0.3 to 0.8 mm.

The amount of phosphorus-containing alumina component present (as the oxide) in the catalyst can range from about 10 to 70 mass percent and preferably from about 20 to 50 mass percent. The aluminum phosphate binder/matrix optionally may contain lesser proportions of other inorganic oxides including, but not limited to, magnesia, beryllia, boria, silica, germania, tin oxide, zinc oxide, titania, zirconia, vanadia, iron oxide, chromia, cobalt oxide and the like which can be added to the hydrosol prior to dropping.

The aluminum-phosphate binder generally is amorphous, i.e., the binder material is essentially of amorphous character. Preferably less than about 10 mass-% of the binder pore volume is micropore volume, characteristic of crystalline material, and the micropore volume more preferably is less than 5% and optimally less than 2% of the pore volume. Crystalline aluminophosphate generally is unsuitable binder material for preparing a strong, crush-resistant catalyst. Material that is not in an amorphous phase generally is present as gamma-alumina; as the phosphorus content of amorphous aluminum phosphate is decreased, therefore, the proportion of crystalline material is increased. The average bulk density of the spheres also varies with the phosphorus content, as a higher proportion of phosphorus decreases the average bulk density. Surface area also is controlled by phosphorus content: gamma-alumina oil-dropped spherical particles typically have surface areas up to about 250 $m^2/g$, while spheroidal particles of aluminum phosphate may have surface areas of up to about 450 $m^2/g$. Al/P atomic ratios of the binder/matrix generally range from about 1/10 to 100/1, more typically from about 1/5 to 20/1, and often between about 1:1 and 5:1.

Best results are achieved when the catalyst has an X-ray diffraction pattern showing characteristic intensities of peaks at specified Bragg angle positions. Specifically, the preferred catalyst has an X-ray powder diffraction pattern such that the ratio of peak intensities at respective two$\Theta$ Bragg angle positions of about 48.5:46.5 is at least about 1.1 and the ratio of peak intensities at respective two-$\Theta$ Bragg angle values of about 48.5:47.5 is at least about 1.0. The X-ray pattern may be obtained by standard X-ray powder diffraction techniques, of which a suitable example is described hereinbelow. Typically, the radiation source is a high-intensity, copper-target, X-ray tube operated at 45 KV and 35 mA. Flat compressed powder samples illustratively are scanned in a continuous mode with a step size of 0.030° and a dwell time of 9.0 seconds on a computer-controller diffractometer. The diffraction pattern from the copper K radiation may be recorded with a Peltier effect cooled solid-state detector. The data suitably are stored in digital format in the controlling computer. The peak heights and peak positions are read from the computer plot as a function of two times theta (two-$\Theta$), where theta is the Bragg angle.

It is within the scope of the invention that the catalyst contains a metal component, preferably selected from components of the group consisting of gallium, rhenium and bismuth. Preferably, however, the catalyst consists essentially of a zeolitic aluminosilicate having a pore diameter of from about 5 to 8 Å and an aluminum phosphate binder.

Optionally, the catalyst may be subjected to precoking in order to increase the proportion of paraxylene in the $C_8$ aromatics product. Precoking of the present catalyst effects a proportion of paraxylene in the product above equilibrium levels at disproportionation conditions, preferably at least about 80 mass-% and optimally about 90 mass-% or more of the $C_8$ aromatics. Precoking is effected on fresh or regenerated catalyst prior to its use for disproportionation at precoking conditions comprising usually at one or more of a higher temperature, lower space velocity, and lower hydrogen-to-hydrocarbon ratio relative to the disproportionation conditions. Such operating conditions generally are within the ranges of those disclosed before for disproportionation, with operating temperature generally being higher and preferably being at least about 50° C. higher than the disproportionation temperature. Precoking time ranges from about 0.5 hours to 10 days. Precoking effects a catalyst carbon content of between about 5 and 40 mass-% carbon, and preferably between about 10 and 30 mass-% carbon. A coke-forming feed for precoking may comprise the feedstock as described herein, or other specific hydrocarbons or mixtures preferably comprising aromatics may be used. Further details relative to precoking are disclosed in U.S. Pat. No. 4,097,543, incorporated herein by reference.

A suitable process combination utilizing precoking therefore comprises the following steps:

selectively precoking an oil-dropped spherical catalyst comprising a zeolitic aluminosilicate having a pore diameter of from about 5 to 8 Å and an aluminum phosphate binder by contacting the catalyst with a coke-forming feed at precoking conditions to deposit between about 5 and 40 mass-% carbon on the catalyst to obtain a selectively coked catalyst; and, disproportionating a toluene-containing feedstock by the sequence of contacting the feedstock and hydrogen-rich gas with a selective-hydrogenation catalyst comprising a Group VIII (IUPAC 8-10) metal and a refractory inorganic oxide in a selective-hydrogenation zone at selective-hydrogenation conditions to obtain a stable intermediate; and, contacting the intermediate with an oil-dropped spherical disproportionation catalyst comprising a zeolitic aluminosilicate having a pore diameter of from about 5 to 8 Å and an aluminum phosphate binder in a disproportionation zone at disproportionation conditions to obtain a paraxylene-rich product.

Preferably, the coke-forming feed is the toluene feedstock prior to selective unsaturates removal.

EXAMPLES

The following examples are presented to demonstrate the present invention and to illustrate certain specific embodiments thereof. These examples should not be construed to limit the scope of the invention as set forth in the claims. There are many possible other variations, as those of ordinary skill in the art will recognize, which are within the spirit of the invention.

Example I

An aluminum-phosphate-bound MFI catalyst was prepared according to the following procedure for use in comparative disproportionation tests to illustrate the invention. A first solution was prepared by adding phosphoric acid to an aqueous solution of hexamethylenetetraamine (HMT) in an amount to yield a alumina:phosphorus atomic ratio in the binder of about 4:1. A second solution was prepared by adding an ammonia-exchanged MFI-type zeolite having an Si/Al$_2$ ratio of about 39 to enough alumina sol, prepared by digesting metallic aluminum in hydrochloric acid, to yield a zeolite content in the finished catalyst equal to about 77 mass-%. These two solutions were commingled to achieve a homogeneous admixture of HMT, phosphorus, alumina sol, and zeolite. This admixture was dispersed as droplets into an oil bath maintained at about 93° C. The droplets remained in the oil bath until they set and formed hydrogel spheres having a diameter of about 1.6 mm. The spheres were removed from the oil bath, water washed, air dried, and calcined at a temperature of about 650° C.

Example II

Pilot-plant tests were carried out to determine the advantages of the invention in a disproportionation reaction. A toluene feedstock derived by extraction and fractionation from catalytic reformate had a Bromine Index of 25 and was designated Feedstock A. A portion of the toluene feedstock was treated for olefin removal with 13X and 4A molecular sieves for up to seven weeks at 10 weight hourly space velocity to reduce its Bromine Index to about 1; the treated toluene was designated Feedstock B.

Example III

The two feedstocks of Example II were processed in a substantially identical manner in successive disproportionation tests using the catalyst of Example I. Disproportionation first was effected at a temperature of 461° C. and 4 weight hourly space velocity (WHSV) over an 12-hour normalization period to achieve an initial toluene conversion of about 53%. The catalyst then was precoked at conditions comprising a temperature of about 560° C. and 4 WHSV in the presence of a 0.5:1 hydrogen:hydrocarbon molar ratio in the presence of nitrogen at a 5:1 molar ratio to hydrogen for a period of time sufficient to effect approximately 90 mole-% paraxylene in total xylenes. Disproportionation of pure toluene then was carried out at 2.45 MPa and 4 WHSV in the presence of pure hydrogen at variable temperatures as required to achieve 30% conversion of toluene. Results then were normalized based on pilot-plant correlations to provide a comparative molar ratio of benzene to xylenes in the product at 30% conversion and 90% paraxylenel xylenes.

Example IV

Comparative results from the disproportionation of the two toluene feedstocks were as follows:

|  | Feedstock A | Feedstock B |
| --- | --- | --- |
| Normalization conversion | decline to 51% | steady at 54% |
| Disprop. temp. for 30% conv. | 467° C. | 454° C. |
| Benzene/xylenes, molar* | 1.76 | 1.57 |

*at paraxylene/xylenes ratio of about 89.3%

The toluene feedstock treated to reduce bromine index showed higher stability in the normalization stage, lower temperature requirement to achieve 30% conversion in the selective disproportionation phase, and higher selectivity for xylenes with lower dealkylation to benzene.

We claim:

1. A process combination for the disproportionation of a toluene-containing feedstock comprising the sequence of:

a. removing unsaturates from the feedstock in a selective unsaturates-removal zone to obtain a stable intermediate; and, b. contacting the intermediate with an oil-dropped spherical disproportionation catalyst comprising a zeolitic aluminosilicate having a pore diameter of from about 5 to 8 Å and an aluminum phosphate binder the catalyst having a X-ray powder diffraction pattern such that the ratio of peak intensities at respective two-Θ Bragg angle values of 48.5:46.5 is at least about 1.1 and the ratio of peak intensities at respective two-Θ Bragg angle values of 48.5:47.5 is at least about 1.0 in a disproportionation zone at disproportionation conditions to obtain a paraxylene-rich product.

2. The process combination of claim 1 wherein the selective unsaturates-removal zone comprises clay treating the feedstock at operating conditions including a temperature of from about 150° to 400° C., a pressure of from atmospheric to about 50 atmospheres, and a weight hourly space velocity of from about 1 to 100.

3. The process of claim 1 wherein the selective unsaturates-removal zone comprises an unsaturate impurity selective-hydrogenation zone designed for contacting the feedstock and hydrogen-rich gas with a selective-hydrogenation catalyst comprising a Group VIII (IUPAC 8-10) metal and a refractory inorganic oxide in the zone at selective-hydrogenation conditions.

4. The process of claim 3 wherein the selective-hydrogenation conditions comprise a temperature of from about 30° to 300° C., a pressure of from about 100 kPa to 6 MPa absolute, and a weight hourly space velocity of from about 1 to 40 $hr^{-1}$.

5. The process of claim 1 wherein the disproportionation conditions comprise a temperature of from about 200° to 600° C., a pressure of from about 100 kPa to 6 MPa absolute, and a hourly space velocity of from about 0.2 to 10 $hr^{-1}$.

6. The process of claim 5 wherein free hydrogen is present in the disproportionation zone at a molar ratio to the intermediate of about 0.5 to 10.

7. The process of claim 1 wherein the paraxylene-rich product contains paraxylene in excess of its equilibrium concentration at disproportionation conditions.

8. The process of claim 1 wherein the zeolitic aluminosilicate comprises a pentasil zeolite selected from the group consisting of MFI, MEL, MTW and TON.

9. The process of claim 8 wherein the zeolitic aluminosilicate comprises MFI zeolite.

10. The process of claim 1 wherein the disproportionation catalyst consists essentially of a zeolitic aluminosilicate having a pore diameter of from about 5 to 8 Å and an aluminum phosphate binder.

11. The process of claim 3 wherein the Group VIII (IUPAC 8-10) metal is selected from one or both of platinum and palladium.

12. A process combination for the disproportionation of a toluene-containing feedstock comprising the sequence of:

a. contacting the feedstock and hydrogen-rich gas with a selective-hydrogenation catalyst comprising a Group VIII (IUPAC 8-10) metal and a refractory inorganic oxide in an unsaturate impurity selective-hydrogenation zone at selective-hydrogenation conditions comprising a temperature of from about 30° to 300° C., a pressure of from about 100 kPa to 6 MPa absolute, and a weight hourly space velocity of from about 1 to 40 $hr^{-1}$ to obtain a stable intermediate; and, b. contacting the intermediate with an oil-dropped spherical disproportionation catalyst comprising a zeolitic aluminosilicate having a pore diameter of from about 5 to 8 Å and an aluminum phosphate binder the catalyst having a X-ray powder diffraction pattern such that the ratio of peak intensities at respective two-Θ Bragg angle values of 48.5:46.5 is at least about 1.1 and the ratio of peak intensities at respective two-Θ Bragg angle values of 48.5:47.5 is at least about 1.0 in a disproportionation zone at disproportionation conditions comprising a temperature of from about 200° to 600° C., a pressure of from about 100 kPa to 6 MPa absolute, and a weight hourly space velocity of from about 0.2 to 10 $hr^{-1}$ to obtain a paraxylene-rich product.

13. The process of claim 12 further comprising deposition of between about 5 and 40 mass-% carbon on the catalyst prior to its use for disproportionation of the feedstock.

14. A process combination for the production of paraxylene comprising the steps of:

(a) selectively precoking an oil-dropped spherical catalyst comprising a zeolitic aluminosilicate having a pore diameter of from about 5 to 8 Å and an aluminum phosphate binder by contacting the catalyst with a coke-forming feed at precoking conditions to deposit between about 5 and 40 mass-% carbon on the catalyst to obtain a selectively coked catalyst; and, (b) disproportionating a toluene-containing feedstock by the sequence of:

I. contacting the feedstock and hydrogen-rich gas with a selective-hydrogenation catalyst comprising a Group VIII (IUPAC 8-10) metal and a refractory inorganic oxide in an unsaturate impurity selective-hydrogenation zone at selective-hydrogenation conditions to obtain a stable intermediate; and, II. contacting the intermediate with an oil-dropped spherical disproportionation catalyst comprising a zeolitic aluminosilicate having a pore diameter of from about 5 to 8 Å and an aluminum phosphate binder the catalyst having a X-ray powder diffraction pattern such that the ratio of peak intensities at respective two-Θ Bragg angle values of 48.5:46.5 is at least about 1.1 and the ratio of peak intensities at respective two-Θ Bragg angle values of 48.5:47.5 is at least about 1.0 in a disproportionation zone at disproportionation conditions to obtain a paraxylene-rich product.

15. The process of claim 14 wherein the selective-hydrogenation conditions comprise a temperature of from about 30° to 300° C., a pressure of from about 100 kPa to 6 MPa absolute, and a weight hourly space velocity of from about 1 to 50 $hr^{-1}$.

16. The process of claim 14 wherein the disproportionation conditions comprise a temperature of from about 200° to 600° C., a pressure of from about 100 kPa to 6 MPa absolute, and a weight hourly space velocity of from about 0.2 to 10 $hr^{-1}$.

17. The process of claim 14 wherein the precoking conditions comprise a temperature at least about 50° C. higher than utilized in the subsequent disproportionation zone.

18. The process of claim 14 wherein the coke-forming feed is the toluene-containing feedstock.

* * * * *